(12) United States Patent
Thong

(10) Patent No.: US 7,471,982 B2
(45) Date of Patent: Dec. 30, 2008

(54) VENTRICULAR TACHYARRHYTHMIA PREDICTION AND/OR PREVENTION

(75) Inventor: Tran Thong, Beaverton, OR (US)

(73) Assignee: Oregon Health & Science University, Portland, OR (US)

(*) Notice: Subject to any disclaimer, the term of this patent is extended or adjusted under 35 U.S.C. 154(b) by 601 days.

(21) Appl. No.: 11/177,450

(22) Filed: Jul. 7, 2005

(65) Prior Publication Data
US 2007/0038254 A1 Feb. 15, 2007

(51) Int. Cl.
A61N 1/36 (2006.01)
(52) U.S. Cl. .................................. 607/14; 607/3

(58) Field of Classification Search .................. None
See application file for complete search history.

(56) References Cited

U.S. PATENT DOCUMENTS

| 4,979,110 A | 12/1990 | Albrecht et al. |
| 5,086,179 A | 2/1992 | Powers et al. |
| 2003/0187479 A1* | 10/2003 | Thong ........................ 607/5 |

* cited by examiner

Primary Examiner—Carl H. Layno
Assistant Examiner—Jon-Eric C. Morales
(74) Attorney, Agent, or Firm—Schwabe, Williamson & Wyatt, P.C.

(57) ABSTRACT

Embodiments of the present invention provide apparatuses and methods to predict and/or prevent episodes of ventricular tachyarrhythmia (for example, ventricular tachycardia and/or ventricular fibrillation). A method is provided for predicting an episode of ventricular tachyarrhythmia by detection and analysis of multiple patterns of vagal fatigue during a period of time.

24 Claims, 4 Drawing Sheets

VENTRICULAR TACHYARRHYTHMIA PREDICTION AND/OR PREVENTION

TECHNICAL FIELD

Embodiments of the present invention relate to the fields of life science and medical devices, and, in particular, to methods and apparatus for predicting and/or preventing episodes of ventricular tachyarrhythmia.

BACKGROUND

Ventricular tachyarrhythmia (VTA) are lethal arrhythmia, namely ventricular fibrillation and ventricular tachycardia, which may accelerate into ventricular fibrillation. Drug therapies may be used, but these anti-arrhythmic drugs often have undesirable side effects. Clinical experience has shown that at an acceptable level, these anti-arrhythmic drugs may reduce but not completely eliminate episodes of VTA. An effective device for treating, as opposed to preventing, VTA is the implantable cardioverter defibrillator (ICD). An ICD may be implanted in a patient at risk of sudden cardiac attack, for example, by an episode of VTA. However, an ICD may treat, but does not prevent episodes of VTA.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

DETAILED DESCRIPTION OF EMBODIMENTS OF THE INVENTION

Figure 1:
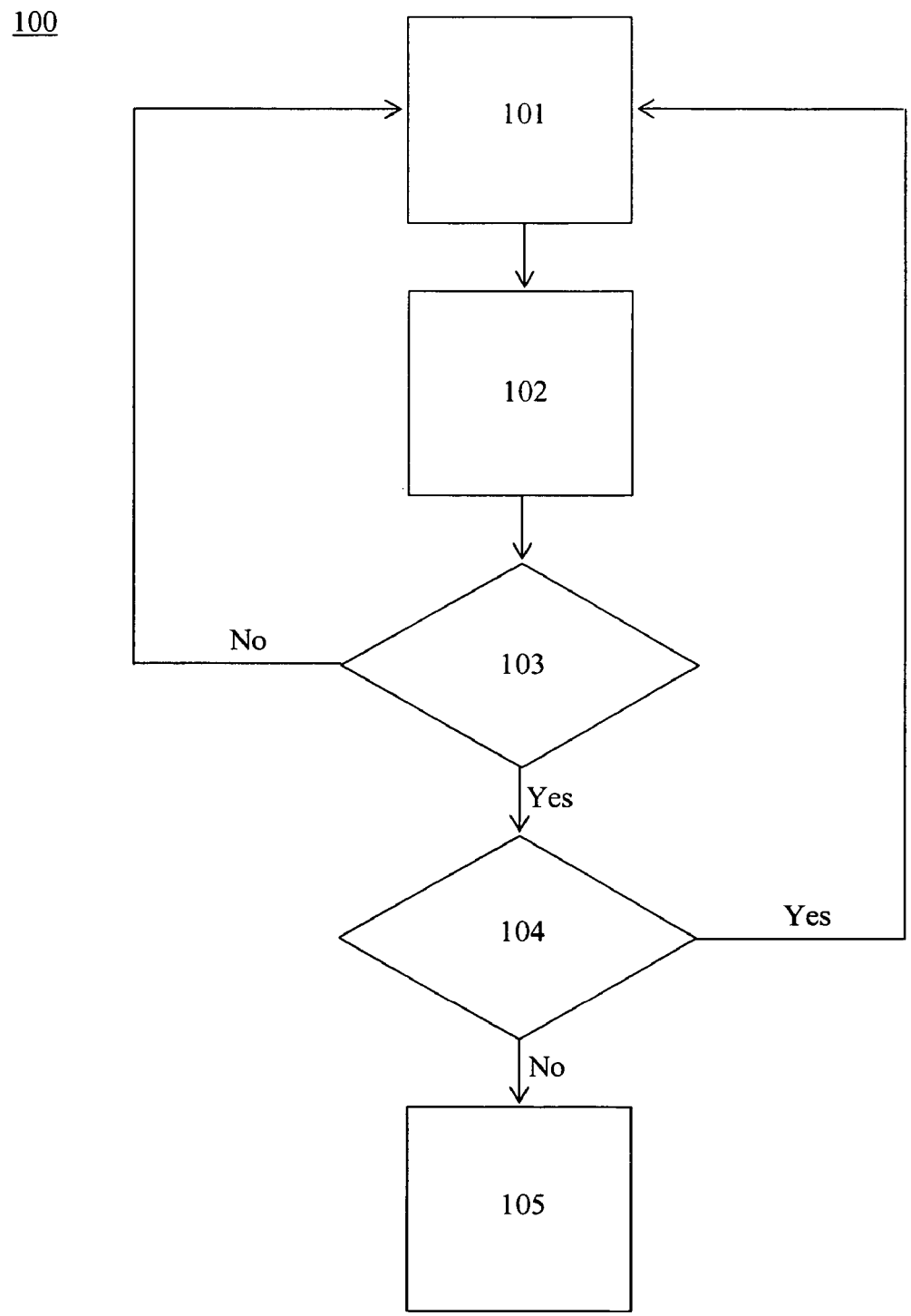
FIG. 1 is a flowchart showing an exemplary method in accordance with an embodiment of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Embodiments of the present invention relate to methods and apparatus for predicting and/or possibly preventing episodes of ventricular tachyarrhythmia and/or providing a warning of an imminent episode of VTA.

Embodiments of the present invention provide apparatus and methods to predict an episode of ventricular tachyarrhythmia (for example, ventricular tachycardia and/or ventricular fibrillation). Embodiments of the present invention may also be used to possibly prevent episodes of ventricular tachyarrhythmia (VTA) by implementing a preventive therapy, such as a temporary pacing regimen, or other suitable procedures. Other embodiments may be used to warn the patient or the medical staff of an imminent episode of VTA.

In an embodiment of the present invention, an implantable defibrillator or similar device may be used to provide preventive therapy in response to a predictor or other indicator of an imminent episode of VTA. An imminent episode is one that may occur within a period of seconds, minutes or hours, such as less than 3 hours from a predefined predictor or indicator.

One indicator of VTA is based on a temporary rhythm acceleration during sinus rhythm termed vagal fatigue pattern (VFP). This pattern is termed VFP because such a rhythm acceleration appears to be a result of a temporary depression of the parasympathetic (vagal) nervous system. Details of VFP and its use for predicting VTA may be found in U.S. Patent Publication No. 2003/0187479, the entire contents and disclosure of which is hereby incorporated by reference. U.S. Patent Publication No. 2003/0187479 provides details related to methods of monitoring and processing R-R intervals (or heart rate), methods of signaling or notifying a patient or medical professional of an imminent VTA, and methods of preventive action in the event an episode of VTA is predicted.

Although R-R intervals are mentioned above, in embodiments of the present invention, the heart rate, P-waves (P-P intervals), or far field measurements may be used in conjunction with or in lieu of the R-R intervals.

According to embodiments of the present invention, performance of a VFP-based VTA prediction algorithm may be measured in part by (1) using the error threshold, which may be for example 4%; (2) computing error from the reference signal, which may be an exponential average of the past R-R intervals (the fraction of the old average may be for example 95%, but may be varied from 90% to 99%); (3) calculating the number of R-R intervals with error above a threshold, such that at a value, which may be, for example 65, it may be determined that a VFP has been detected; and (4) exponentially decaying the R-R counter using, for example, 90% of the previous value, such that when the count reaches a value, which may be for example 5, interval counting is stopped and the VFP indicators are halted to mark the end of a VFP.

According to an embodiment of the present invention, a method is provided for predicting an episode of VTA by detection and analysis of multiple patterns of vagal fatigue during a predefined period of time.

According to embodiments of the present invention, methods of the present invention may also be implemented using hardware, and thus may provide monitoring, prediction, and/or prevention capabilities. Embodiments of the present invention may include fully or partially implantable and/or external devices. Further, embodiments of the present invention may provide for notification of an imminent VTA.

FIG. 1 is a flowchart showing an exemplary method 100 in accordance with an embodiment of the present invention. In block 101, a subject's heart is monitored with a suitable monitoring device (implantable device, ICD, pacemaker, electrode(s), external and/or internal cardiac monitors, electrocardiogram monitor, pulse oximeter with heart rate measurement, etc.), to collect data associated with the subject's heart. The collected data is then processed in block 102 to generate a number of metrics, for example, the R-R interval, heart rate or P-P interval. The metrics are further analyzed to determine whether a VFP exists. At diamond 103, a determination is made whether the analysis suggests that a VFP exists. If a VFP does not exist, the associated devices may continue to monitor the heart without initiating further action. In an embodiment of the present invention, the monitoring devices may continuously monitor the status of the heart independent of any analysis, processing or other action. If a VFP does exist, a second determination is made at diamond 104. At diamond 104, a determination is made whether a predefined amount of time has expired since the previous occurrence of a VFP was detected. If a predefined amount of time has expired, the associated devices may continue to monitor the heart without initiating further action. If a predefined amount of time has not expired, a multiple-VFP condition exists and further action may be initiated at block 105. Such further action may include providing a warning or notification of a multiple-VFP condition and/or initiating action such as preventive pacing therapy to attempt to prevent a VTA from occurring. In an embodiment of the present invention, prior to initiating action, the method may optionally first provide for a determination of the current status of the heart to determine whether the heart is currently experiencing a VTA. In such a situation, preventive therapy would typically not be useful, and thus may be avoided.

A multiple-VFP condition refers to the occurrence of more than one VFP within a predefined period of time. In embodiments of the present invention, a method may be used to detect a minimum of 2, 3, 4, or more VFPs during a defined period of time. The period of time may be defined by a user based on the particular subject/patient, historical and/or statistical data. According to embodiments of the present invention, a suitable predefined period time in which the occurrence of multiple-VFPs may be used to indicate a condition of concern may be, for example, less than 5 hours, less than 3 hours, less than 2 hours, less than 1 hour, less than 30 minutes, etc.

Embodiments of the present invention provide prediction of VTAs with a sensitivity of at least approximately 30%, for example at least approximately 40%, preferably at least approximately 45%, a specificity of at least approximately 80%, for example at least approximately 90%, preferably at least approximately 95%, and a type II error rate of less than approximately 3 events per day, preferably less than approximately 1 event per day. For the purposes of various embodiments of the present invention, the term sensitivity refers to the percentage of accurately identified episodes of VTA based on detection of one or more VFP. For the purpose of various embodiments of the present invention, the term specificity refers to the percentage of periods of time, without VTA, of duration comparable to those used to determine sensitivity, that are correctly classified by the method as without VFP. For the purposes of various embodiments of the present invention, the term type II error rate refers to the rate of VFPs detected, whether single or multiple, depending on the detection criterion used, that are not followed by a VTA during the specified time period. For the purposes of various embodiments of the present invention, the term R-R interval refers to the duration between two consecutive R waves of an electrocardiogram.

Figure 2:
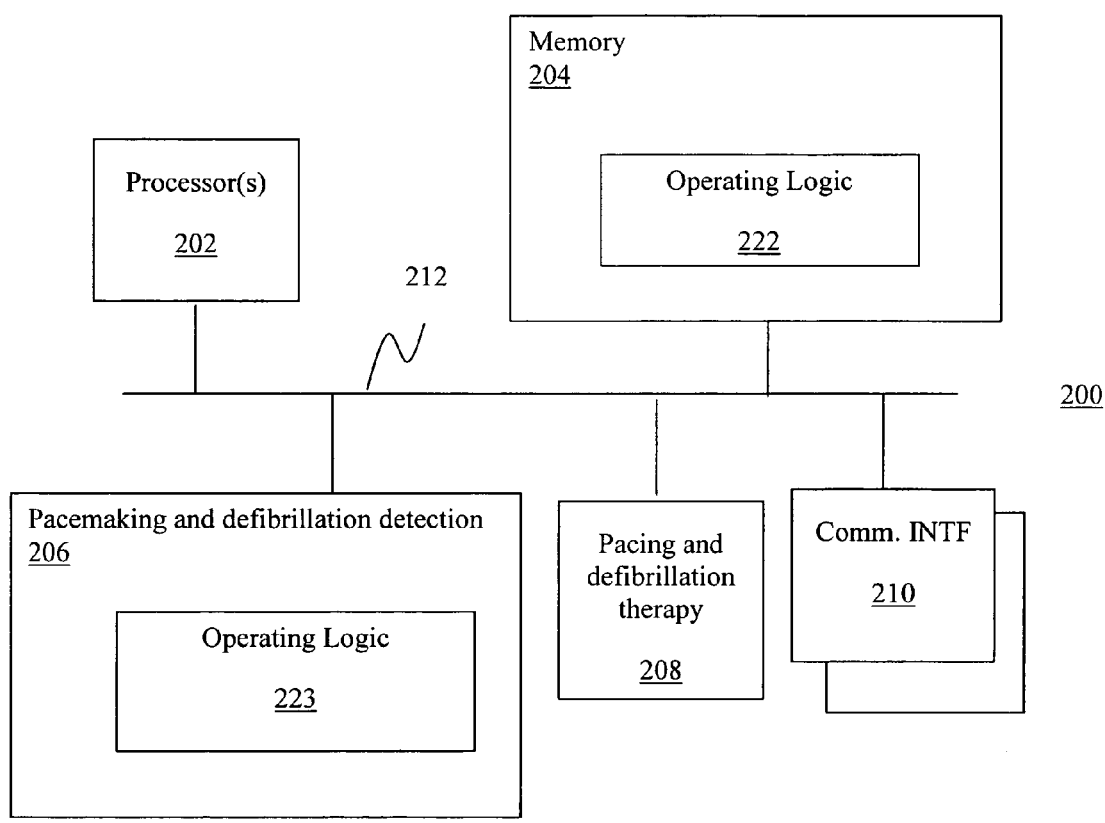
FIG. 2 illustrates an exemplary computing device suitable for use in accordance with various embodiments of the present invention.

FIG. 2 illustrates a block diagram view of an exemplary computing device suitable for use in one or more of the embodiments of the present invention. As illustrated, computing device 200 includes processor 202, memory 204 coupled to each other via bus 212. Further, computing device 200 also includes pacemaking and defibrillation detection circuits 206 with operating logic 223, pacing and defibrillation therapy 208, and communication interface 210 coupled to the earlier described elements as shown.

Each of the elements represents a broad range of the corresponding element known in the art or to be designed consistent with the teachings of the embodiments of the present invention. They perform their conventional functions, i.e. processing, storage, and so forth. In particular, memory 204 may be employed to store temporal and persistent copies of operating logic 222, which may be adapted to practice all or selected aspects of the various methods of the various embodiments of the present invention.

In various embodiments of the present invention, communication interface 210 may include mechanisms for communication from inside the body to an external device, as is known in the art, for example, of pacemakers and ICDs. In various embodiments of the present invention, computing device 200 may be an ICD or pacemaker, which may be linked to an external desktop computer, a tablet computer or a palm sized computing device through communication interface 210. The external link may be occasional, for example during follow-up, or continual, for example through a radio-frequency or electromagnetic coupling link.

EXAMPLES

The following R-R histories (A, B and C) were analyzed for VFP: A) Twenty-three 24-hour Holter records from one set of subjects referred to as the VA-ICD data set. Each subject had ICD implanted prior to beginning the study. Each subject wore a Holter monitor for 24 hours. No episode of VTA was detected during Holter monitoring. B) 208 records from Biotronik ICDs. The average record length was about 1.6 hours prior to an episode of VTA. This is referred to as the Bio-ICD data set. This data set does not include records during which the subject was either bradycardic or had an episode of atrial tachyarrhythmia. C) Seven 24-hour Holter records of normal subjects from the MIT-BIH "long term" data base. This is referred to as the MIT-BIH data set.

In these examples, all VFP episodes that occur within a sliding window of 65 R-R intervals long (~40 s) are considered to be part of one episode. While a number of parameters may be used to optimize the performance of a VFP-based VTA prediction algorithm, the duration threshold is used in these examples.

Using the VA-ICD data set, random records may be created that match the Bio-ICD data set in record length. For each of these surrogate-VA-ICD records, a random VA-ICD record and a random starting point may be selected. If VTA episodes are independent of VFP episodes, then one may expect to have about the same number of records exhibiting VFP episodes in both the Bio-ICD and the surrogate-VA-ICD data sets. The results of this exemplary study are summarized in Table 1.

TABLE I

Incidence of vagal fatigue in the actual Bio-ICD data set and record length matching surrogate-VA-ICD data set.

| Duration Threshold | Bio-ICD | Surrogate-VA-ICD |
| --- | --- | --- |
| 65 | 42.3% | 6.5% |
| 50 | 61.1% | 17.7% |

Statistically, with p <<0.05, the two distributions are different. Thus, it appears that episodes of VFP are associated more frequently (~6.5× in this example) with episodes of VTA in the ICD population.

Figure 3:
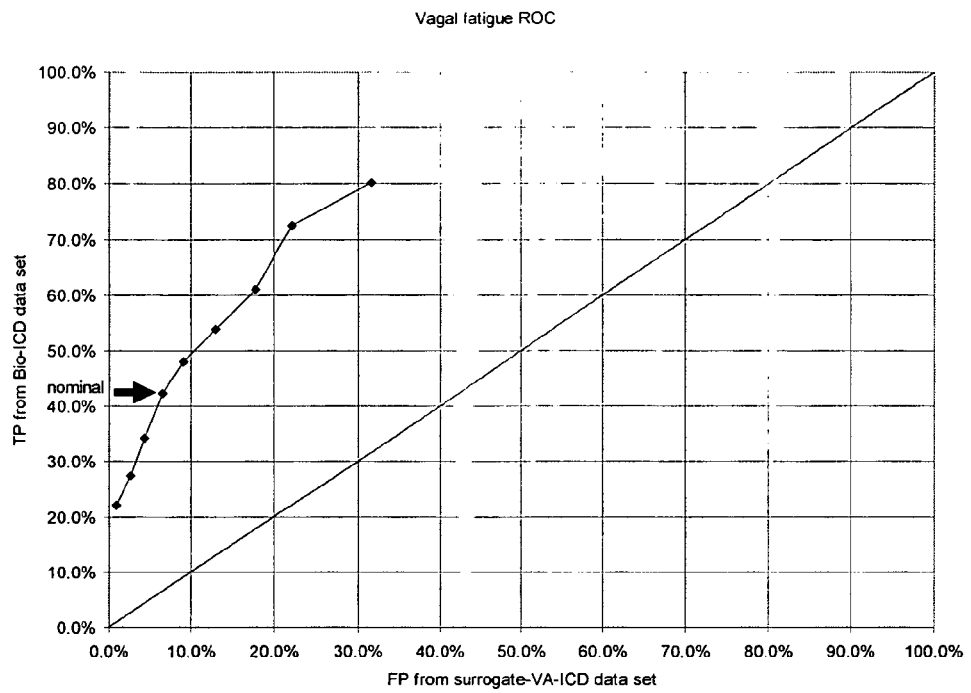
FIG. 3 shows a receiver operating curve (ROC) of vagal fatigue prediction of a ventricular tachyarrhythmia (VTA) based on Bio-ICD and surrogate-VA-ICD data sets.

While the records in the surrogate-VA-ICD data set may not be strictly independent, one may assume that the original VA-ICD data set is representative of ICD wearers during non-VTA periods, and thus the surrogate-VA-ICD data set may be considered a record-matched data set from which one may determine the approximate specificity of the VFP indicator. By varying the duration threshold value, one may arrive at the receiver operating curve (ROC) shown in FIG. 3.

Figure 4:
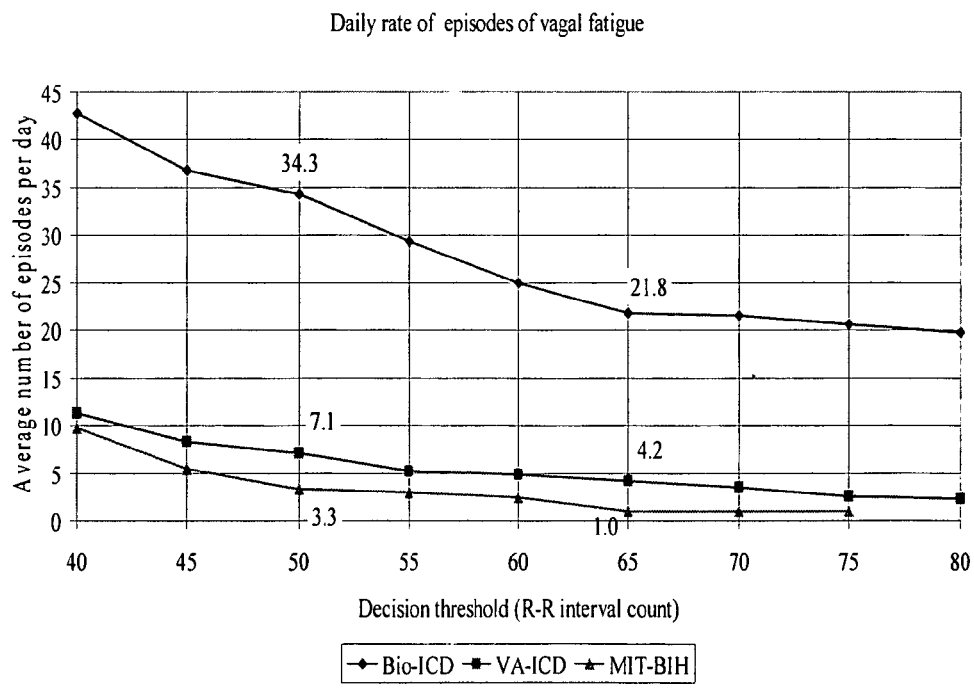
FIG. 4 is a graph plotting daily rate of vagal fatigue episodes as a function of duration threshold.

At the duration threshold of 65 R-R intervals, the sensitivity is approximately 40-45% (42.3% from Table 1), and the specificity is 93.5% (6.5% false positive from Table 1). In embodiments of the present invention, a more meaningful measure than the specificity may be the daily (24 hour) rate of VFP in the VA-ICD population, which is effectively the type II error rate, with the assumption that the VA-ICD data set is representative of the non-VTA condition. This is shown in FIG. 4. At the duration threshold of 65 R-R intervals, the type II error rate based on the VA-ICD data set, is only 4.2 events daily in the subjects with VFP, 1.8 events/day in the overall population.

Methods in accordance with embodiments of the present invention may provide increased sensitivity and/or a decreased rate of type II error. One way to increase sensitivity may be to decrease the duration threshold. For example, going from 65 R-R intervals to 50 R-R intervals, the sensitivity as shown in Table 1 may increase from 42.3% to 61.1%. From Table 1, going from 65 R-R intervals to 50 R-R intervals, the specificity decreases from 93.5% to 82.3%. The rate of type II error, as shown in FIG. 4, increases from 4.2 events/day to 7.1 events/day, in subjects with episodes of VFP.

If, in addition to reducing the duration threshold, a rate of VFP corresponding to multiple events over a defined period of time is used as part of the VTA prediction method, the type II error rate may be decreased with a corresponding increase in specificity.

For example, according to an embodiment of the present invention, a rate of VFP corresponding to 2 events in a period of less than 2 hours, for example 1.8 hours, may provide a reduction in the type II error rate as described in these examples.

Figure 5:
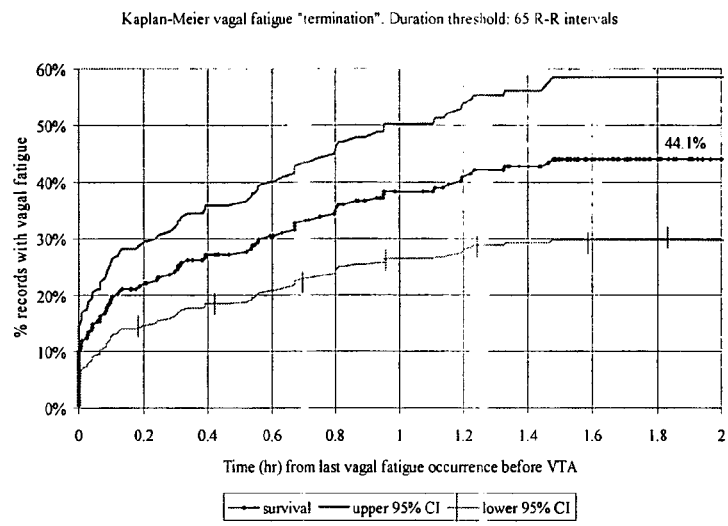
FIG. 5 shows a Kaplan-Meier termination curve for vagal fatigue prior to ventricular tachyarrhythmia (VTA)
Figure 6:
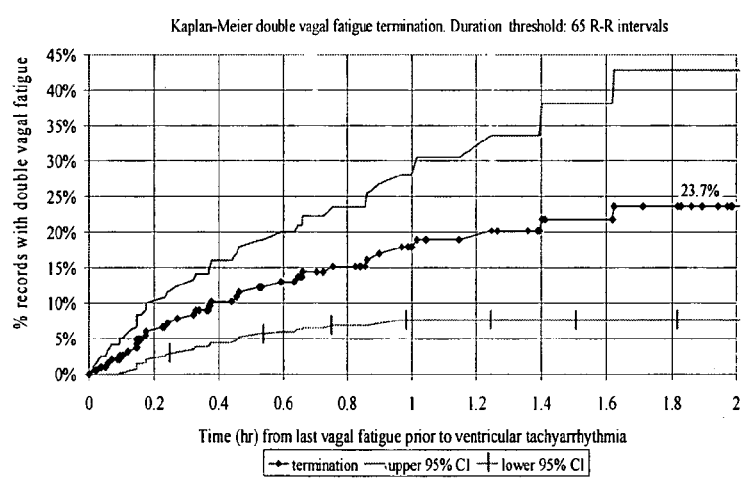
FIG. 6 shows a Kaplan-Meier curve for double vagal fatigue for a duration threshold of 65 R-R intervals.

Considering the Bio-ICD records, at a duration threshold of 65 R-R intervals, with at least one VFP within 1.8 hours from the VTA, one may derive a Kaplan-Meier termination curve for the prior VFP event. This is shown in FIG. 5. A total of 44.1% of the records have a VFP within 1.8 hour from the VTA. Next consider those Bio-ICD records, with at least one VFP prior to the VTA. The Kaplan-Meier termination curve for those with two prior VFPs within the indicated time is shown in FIG. 6. Thus, the double VFP sensitivity for these examples is 23.7%. The double VFP specificity in these examples was found to be ~100% (no double VFP in the surrogate-VA-ICD data set). The type II error rate reduces to (10 events in VA-ICD data set) 0.44 event/day.

Figure 7:
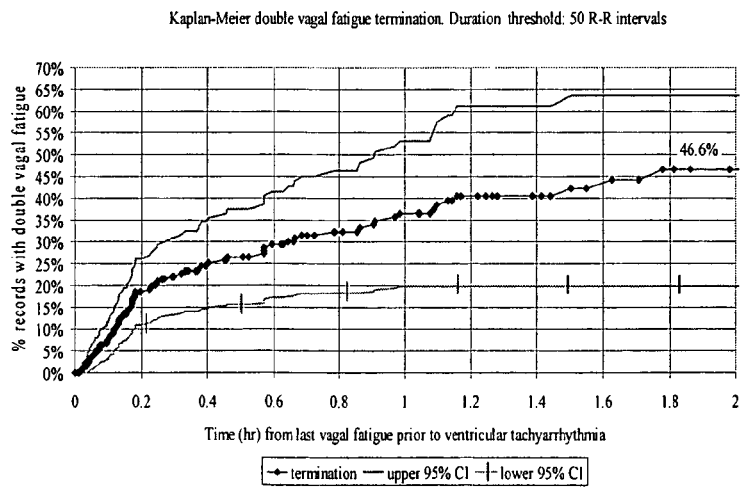
FIG. 7 shows a Kaplan-Meier termination curve for double vagal fatigue prior to ventricular tachyarrhythmia (VTA) for a duration threshold of 50 R-R intervals.

Reducing the duration threshold to, for example, 50 R-R intervals, the corresponding double VFP sensitivity becomes 46.6% in these examples, as shown in FIG. 7. The double VFP specificity is found to be 95.2% (10 false positives/208 records in the surrogate-VA-ICD data set). The type II error rate (16 double VFP episodes in the VA-ICD data set) becomes 0.7 event/day.

Thus, in the present examples, using an observation time of 1.8 hour, a sensitivity of 47% for predicting an imminent episode of VTA may be achieved with a type II error rate of only 0.7 event/day (and associated specificity of 95%), using a double vagal fatigue method in accordance with an embodiment of the present invention. In these examples, a VTA may be expected within 1.8 hour from the double vagal fatigue event.

Embodiments of the present invention provide methods for predicting VTA as well as possibly preventing episodes of VTA from occurring. Embodiments of the present invention may be incorporated into or combined with preventive therapies and devices, such as a pacemaker, ICD, and/or various anti-arrhythmic drugs to provide systems for predicting and possibly preventing VTA.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method for predicting an occurrence of ventricular tachyarrhythmia in a subject, comprising:
    detecting for a first pattern of vagal fatigue exhibited by the subject; and
    detecting for at least one additional pattern of vagal fatigue exhibited by the subject prior to expiration of a period of time after detecting said first pattern of vagal fatigue and prior to an occurrence of ventricular tachyarrhythmia in the subject, wherein the detections of said first pattern and said at least one additional pattern of vagal fatigue within said period of time are performed to facilitate prediction of the occurrence of ventricular tachyarrhythmia in the subject.

2. The method of claim 1, wherein the method further comprises selecting said period of time to be less than 3 hours.

3. The method of claim 1, wherein the method further comprises selecting said period of time to be less than 2 hours.

4. The method of claim 1, wherein said detections are performed to facilitate prediction of an imminent occurrence of ventricular tachyarrhythmia.

5. The method of claim 1, wherein said detections are performed to facilitate prediction of an occurrence of ventricular tachyarrhythmia predicted to occur in less than 3 hours.

6. The method of claim 1, wherein said detections are performed to facilitate prediction of an occurrence of ventricular tachyarrhythmia predicted to occur in less than 2 hours.

7. The method of claim 1, wherein said detections are performed to facilitate prediction of an occurrence of ventricular tachyarrhythmia predicted to occur in less than 30 seconds.

8. The method of claim 1, wherein the method has a specificity of at least approximately 90%.

9. The method of claim 1, wherein the method has a specificity of at least approximately 95%.

10. The method of claim 1, wherein the method results in a Type II error rate of less than approximately 3 events per day.

11. The method of claim 1, wherein the method results in a Type II error rate of less than approximately 1 event per day.

12. A method for preventing an occurrence of ventricular tachyarrhythmia in a subject, comprising:

predicting for an occurrence of ventricular tachyarrhythmia in said subject based at least in part on at least two detected vagal fatigue patterns exhibited by the subject during a time prior to an occurrence of tachyarrhythmia; and initiating at least one preventive action to prevent said predicted occurrence of ventricular tachyarrhythmia from occurring.

13. The method of claim 12, wherein said initiating of a preventive action comprises providing a warning or notification of said predicted occurrence of ventricular tachyarrhythmia.

14. The method of claim 12, wherein said initiating of a preventive action comprises initiating a preventive cardiac pacing therapy.

15. The method of claim 12, wherein said initiating of a preventive action comprises providing at least one anti-arrhythmic drug to said subject.

16. The method of claim 12, wherein the method further comprises determining whether said subject is experiencing a ventricular tachyarrhythmia, prior to said initiating of a preventive action.

17. The method of claim 12, wherein the method further comprises selecting said period of time to be less than 3 hours.

18. The method of claim 12 wherein the method further comprises selecting said period of time to be less than 2 hours.

19. An apparatus comprising:

a cardiac monitor configured to detect at least two vagal fatigue patterns exhibited by a subject during a time period prior to an occurrence of ventricular tachyarrhythmia; and a processor, coupled to the cardiac monitor, is programmed to receive from said cardiac monitor data indicative of detected vagal fatigue pattern, and to predict an occurrence of ventricular tachyarrhythmia in the subject, based at least in part on the received data.

20. The apparatus of claim 19, wherein said cardiac monitor comprises an implantable cardioverter defibrillator, a pacemaker, or an external cardiac monitor.

21. The apparatus of claim 19, wherein the apparatus further comprises a device coupled to the processor and configurable to be controlled by the processor to take a preventive action to prevent a predicted occurrence of ventricular tachyarrhythmia in the subject from occurring.

22. The apparatus of claim 21, wherein said device comprises an implantable cardioverter defibrillator or an implantable drug delivery device.

23. An apparatus comprising:

A processor programmed to receive data indicative of at least two detected vagal fatigue patterns exhibited by a subject during a time period prior to an occurrence of ventricular tachyarrhythmia, and to predict an occurrence of ventricular tachyarrhythmia in the subject, based at least in part on the received data; and a device coupled to the processor and configurable to be controlled by the processor to take a preventive action to prevent a predicted occurrence of ventricular tachyarrhythmia in the subject occurring.

24. The apparatus of claim 23, wherein said device comprises an implantable cardioverter defibrillator or an implantable drug delivery device.

* * * * *